(12) United States Patent
Pouget et al.

(10) Patent No.: US 6,966,898 B1
(45) Date of Patent: Nov. 22, 2005

(54) SAFETY DEVICE FOR AN INJECTION SYRINGE

(75) Inventors: Michel Pouget, Domarin (FR); Fabrice Bonacci, Saint Priest (FR)

(73) Assignee: Compagnie Plastic Omnium, Lyons (FR)

( * ) Notice: Subject to any disclaimer, the term of this patent is extended or adjusted under 35 U.S.C. 154(b) by 260 days.

(21) Appl. No.: 10/111,137

(22) PCT Filed: Oct. 26, 2000

(86) PCT No.: PCT/FR00/02986

§ 371 (c)(1),
(2), (4) Date: Jul. 29, 2002

(87) PCT Pub. No.: WO01/30427

PCT Pub. Date: May 3, 2001

(30) Foreign Application Priority Data

Oct. 26, 1999 (FR) .................................. 99 13348

(51) Int. Cl.[7] .............................................. A61M 5/32
(52) U.S. Cl. ...................................... 604/197; 604/198
(58) Field of Search ........................ 604/110, 263, 187, 604/192, 195, 197, 198, 156, 264

(56) References Cited

U.S. PATENT DOCUMENTS

| | | | | |
|---|---|---|---|---|
| 5,163,918 A | * | 11/1992 | Righi et al. | 604/198 |
| 5,562,626 A | * | 10/1996 | Sanpietro | 604/110 |
| 6,186,980 B1 | * | 2/2001 | Brunel | 604/110 |
| 6,626,864 B2 | * | 9/2003 | Jansen et al. | 604/110 |

FOREIGN PATENT DOCUMENTS

| | | |
|---|---|---|
| EP | 1 090 653 | 4/2001 |
| WO | WO 00/76565 | 12/2000 |
| WO | WO 01/24856 | 4/2001 |

* cited by examiner

*Primary Examiner*—Nicholas D. Lucchesi
*Assistant Examiner*—Matthew DeSanto
(74) *Attorney, Agent, or Firm*—Oliff & Berridge, PLC

(57) ABSTRACT

A safety device for a syringe constituted by a body, a needle carrier mounted at one end of the body, a piston that is axially movable in the body, and a piston plunger projecting from the body at its end opposite from the needle carrier and suitable for pushing the piston inside the body towards the needle carrier, the device comprising a sheath in which the syringe body can slide axially between an injection position in which the needle carrier is flush with one end of the sheath and a safe position in which the needle carrier is retracted into the sheath, a helical spring which is axially compressed when the syringe body is in the injection position, said spring then exerting on said body a force tending to cause it to slide into the safe position, retention means for retaining the syringe body in the injection position, and a release mechanism for releasing the retention means acting on said retention means when the piston plunger of the syringe has pushed the piston inside the body into the vicinity of the needle carrier, wherein the retention means for retaining the body of the syringe in the injection position in the sheath are constituted by at least one radially-movable resilient tab extending substantially longitudinally relative to the sheath and arranged to hold the spring in the compressed state even when the syringe body is not in the sheath.

2 Claims, 6 Drawing Sheets

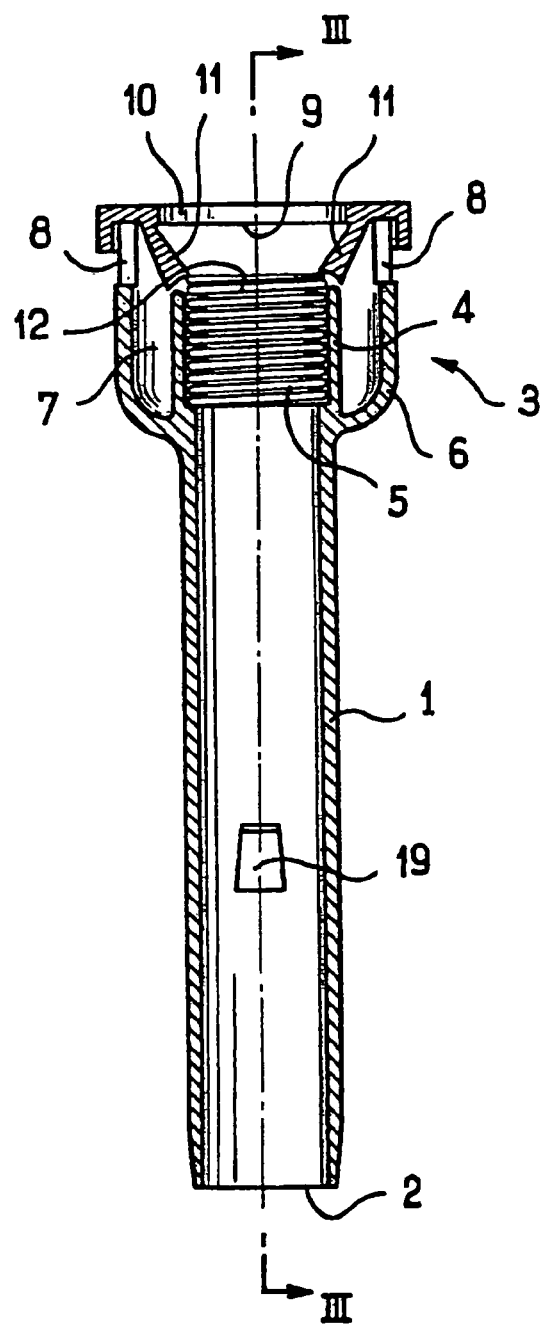
FIG_1
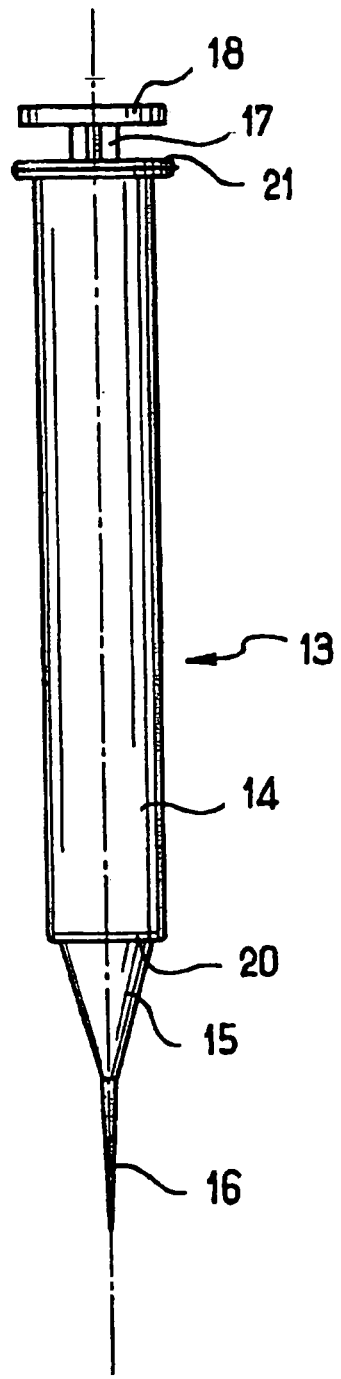
FIG_2

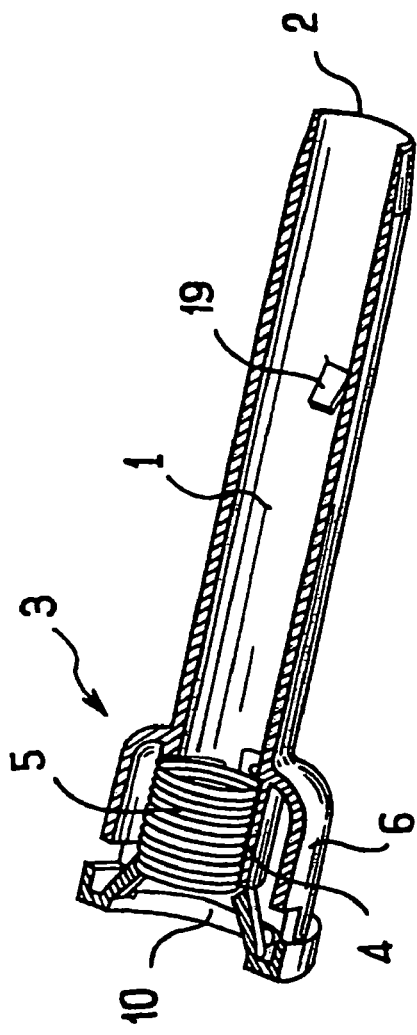
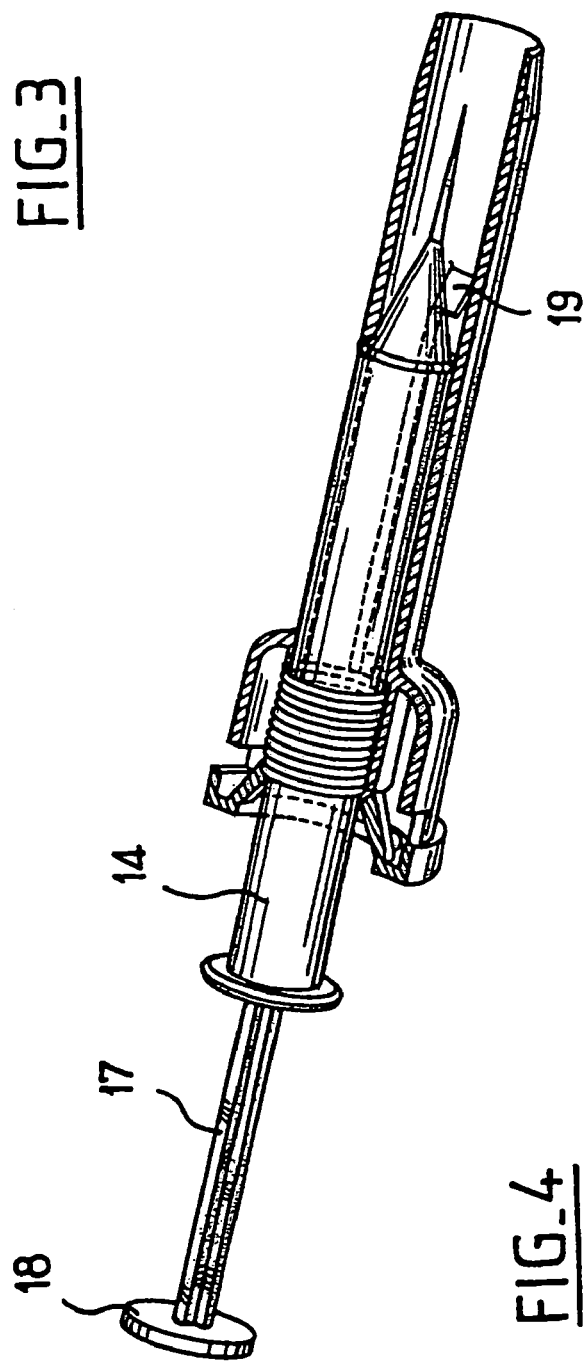

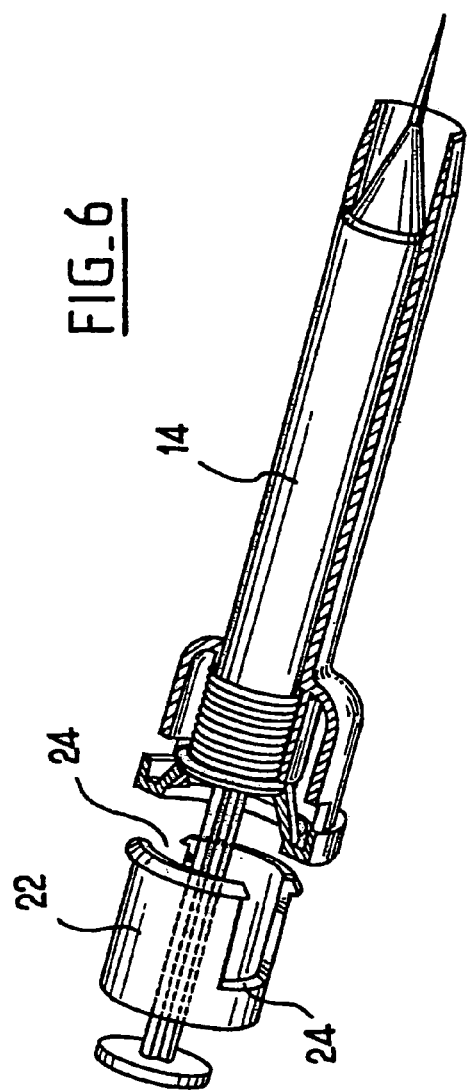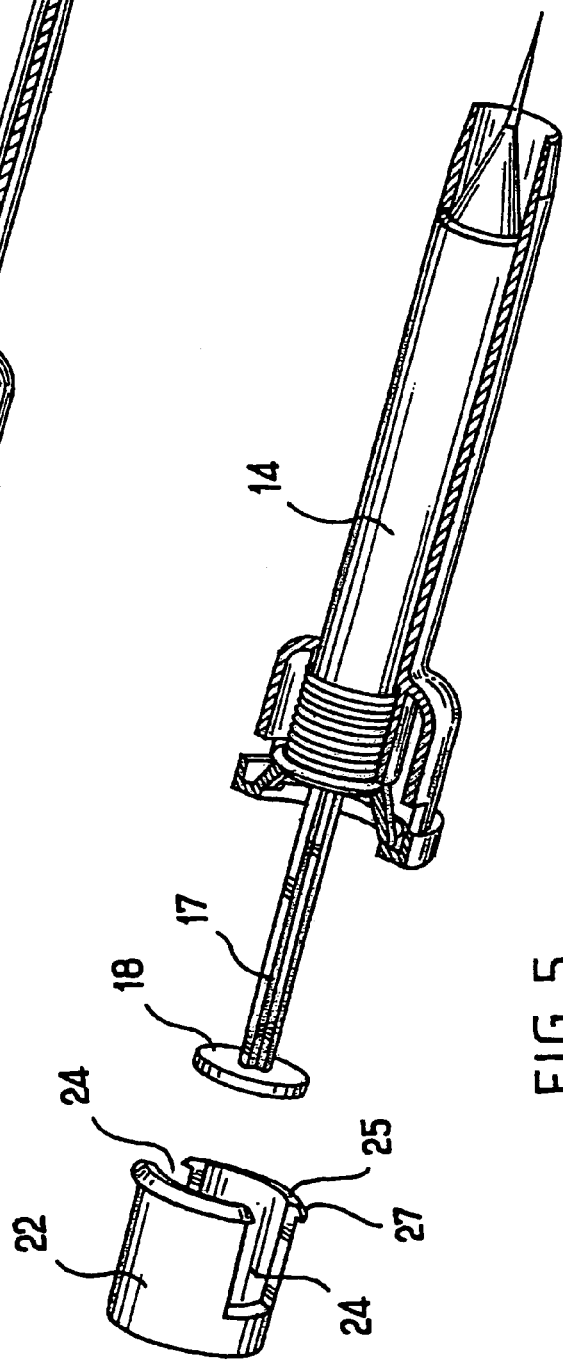

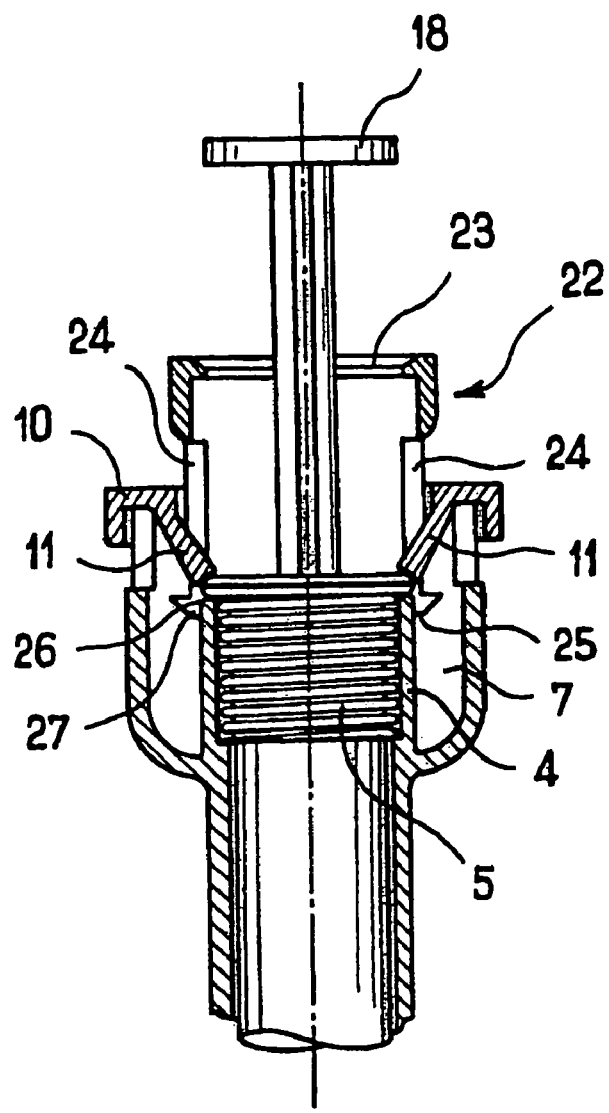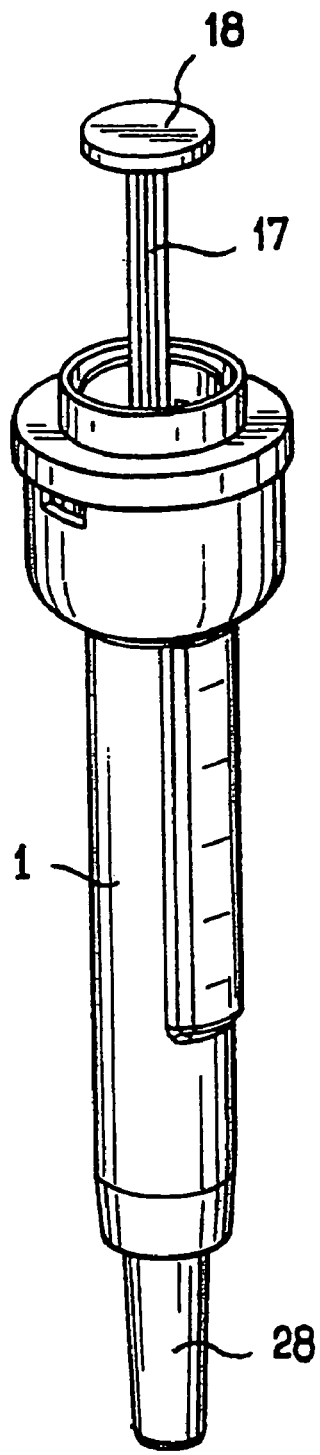
FIG_7
FIG_8

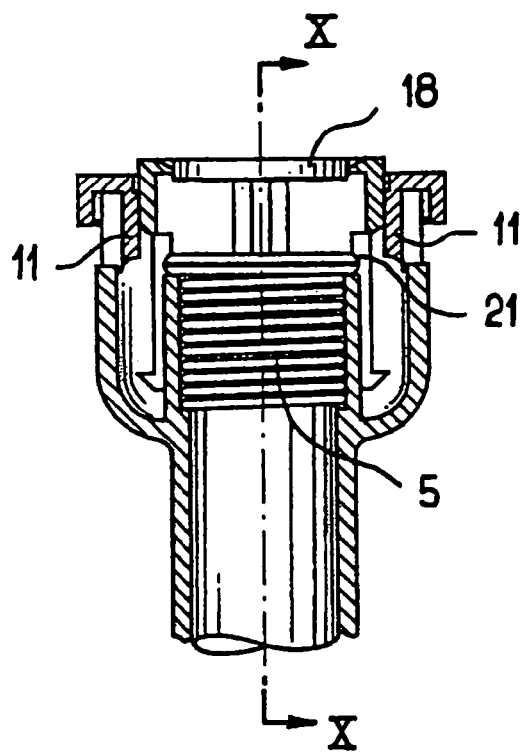
FIG_9
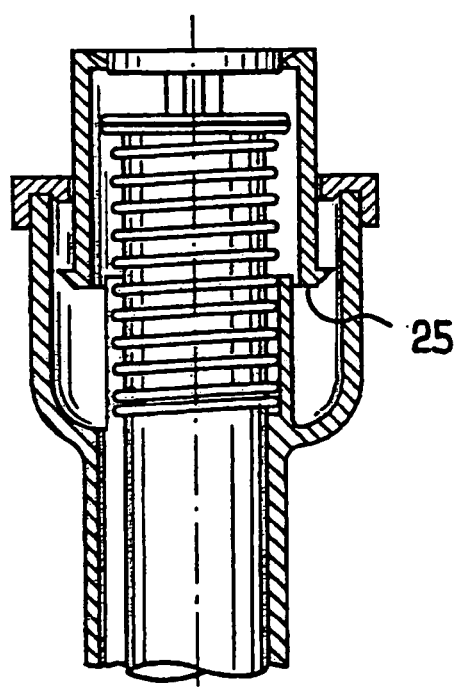
FIG_10
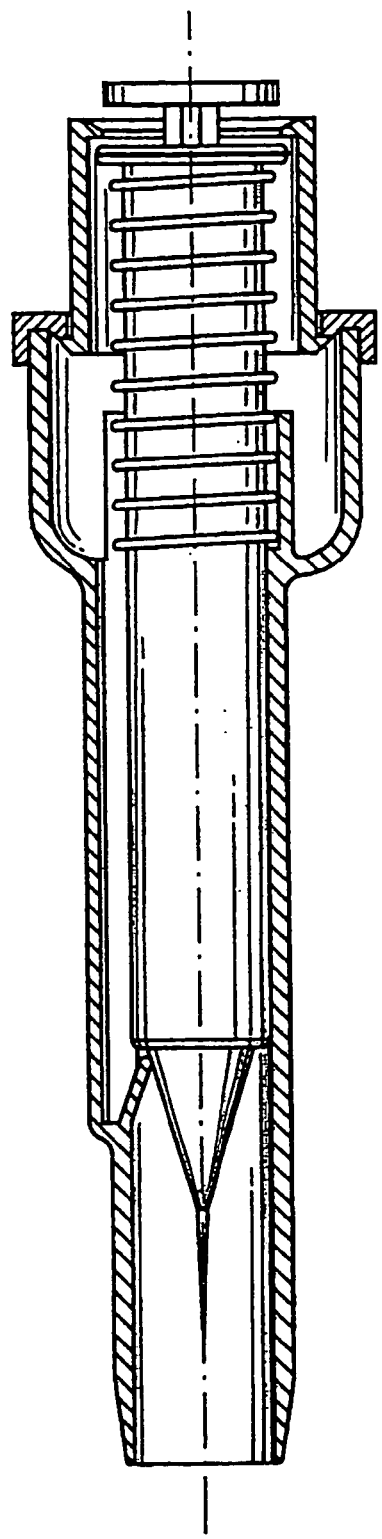
FIG_11

SAFETY DEVICE FOR AN INJECTION SYRINGE

The present invention relates to a safety device for an injection syringe.

BACKGROUND OF THE INVENTION

It is known that certain injectable medicines are distributed as doses in syringe bodies that are filled in advance, and to which it suffices merely to add piston plungers and needles in order to transform them into syringes.

It is also known that syringes constitute instruments that are dangerous, in particular for medical personnel, because after use, their dirty and potentially contaminated needles can accidentally touch or prick people and contaminate them.

OBJECTS AND SUMMARY OF THE INVENTION

The present invention seeks to provide a safety device to avoid that kind of accident happening.

The present invention provides a safety device for a syringe constituted by a body, a needle carrier mounted at one end of the body, a piston that is axially movable in the body, and a piston plunger projecting from the body at its end opposite from the needle carrier and suitable for pushing the piston inside the body towards the needle carrier, the device comprising a sheath in which the syringe body can slide axially between an injection position in which the needle carrier is flush with one end of the sheath and a safe position in which the needle carrier is retracted into the sheath, a helical spring which is axially compressed when the syringe body is in the injection position, said spring then exerting on said body a force tending to cause it to slide into the safe position, retention means for retaining the syringe body in the injection position, and a release mechanism for releasing the retention means acting on said retention means when the piston plunger of the syringe has pushed the piston inside the body into the vicinity of the needle carrier, wherein the retention means for retaining the body of the syringe in the injection position in the sheath are constituted by at least one radially-movable resilient tab extending substantially longitudinally relative to the sheath and arranged to bold the spring in the compressed state even when the syringe body is not in the sheath.

By means of the safety device of the invention, the substance contained in the syringe can be injected into a patient in the same manner as if the syringe were used on its own, so long as the syringe body is in the injection position, in which position the needle mounted on the needle carrier of the syringe projects beyond the sheath.

When the piston comes into the vicinity of the needle carrier, i.e. at the end of injecting the substance, the release mechanism acts on the locking means and releases the syringe body, which, under thrust from the spring, slides inside the sheath so as to reach its safe position in which the needle carrier is withdrawn and the needle no longer projects from the sheath.

In this safe position, which the needle body reaches only after injection has ended, all risk of accidental injury by contact with the dirty needle is avoided since the needle is retracted inside the sheath and is no longer accessible.

The device of the invention is particularly adapted to use with prefilled syringes since the syringe body is put into place inside the sheath while the spring is maintained in the compressed state by the retention means.

In other words, the user does not need to compress the spring when engaging the syringe body in the sheath.

This greatly facilities use of the device of the invention.

The lack of any need to provide force for compressing the spring at the time the syringe body is inserted also makes it possible to automate assembly of prefilled syringe bodies in safety devices of the invention.

In a particular embodiment of the invention, the helical spring is received inside the sheath in an enlarged portion thereof, around the syringe body, and it bears both against a bearing surface of the sheath and against a collar of the syringe body.

In this embodiment, the release mechanism is constituted by a cap sliding in the sheath and which moves inside the sheath towards the resilient tab to move it radially away so as to release the syringe body and/or the spring.

The ring is moved when the piston reaches the vicinity of the needle carrier inside the syringe body.

This result is obtained by dimensioning the sheath in such a manner that the user's finger comes into contact with the ring at the end of the piston stroke, i.e. at the end of injection.

Thus, at the end of the stroke of the piston plunger, the user pushes in the ring, thereby moving away the resilient tab, which releases the syringe body allowing it to rise inside the sheath, thereby retracting the needle into said sheath.

BRIEF DESCRIPTION OF THE DRAWINGS

In order to make the invention better understood, there follows a description of two embodiments given as non-limiting examples, with reference to the accompanying drawings, in which:

FIG. 1 is an axial section view of a safety device;

FIG. 2 is an elevation view of a syringe;

FIG. 3 is a view in perspective and in section on III—III of FIG. 1;

FIG. 4 is a view analogous to FIG. 3, showing the syringe while it is in being inserted into the sheath;

FIG. 5 is a view analogous to FIG. 4 showing the syringe engaged in the sheath;

FIG. 6 is a view analogous to FIG. 5 showing a cap of the sheath being put into place on the sheath;

FIG. 7 is a view on a larger scale showing the top portion of the sheath fitted with the cap;

FIG. 8 is a perspective view of the device ready for use;

FIG. 9 is a view analogous to FIG. 7, showing the device when the piston plunger reaches the end of its stroke under thrust exerted by a user's finger;

FIG. 10 is a section view on X—X of FIG. 9, showing the device when the user's finger releases the pressure;

FIG. 11 is a section view analogous to FIG. 10, showing the device after it has been used.

MORE DETAILED DESCRIPTION

Figure 12:
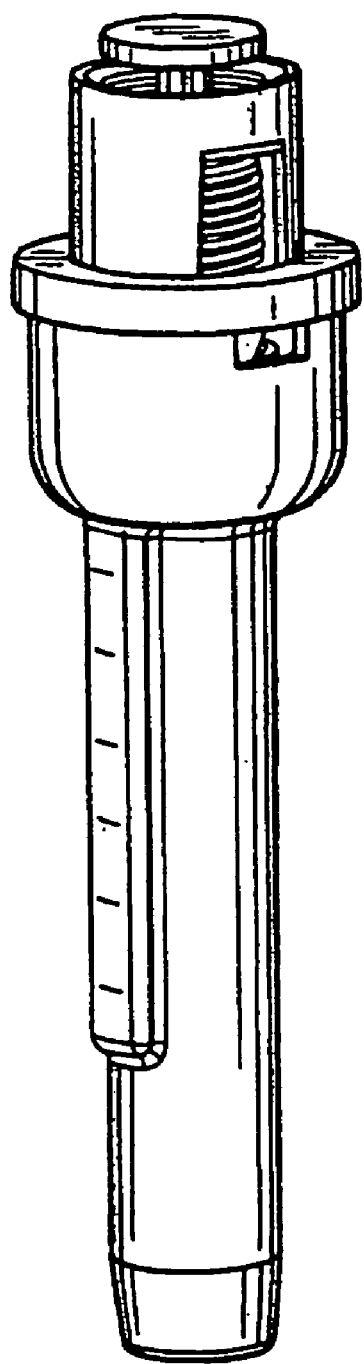
FIG. 12 is a perspective view showing the device after use.

The sheath of the safety device shown in FIG. 1 comprises a cylindrical portion 1 having a bottom opening 2 and at its end opposite from said opening 2, a head 3 constituted both by a tubular portion 4 which contains a helical spring 5 extending the inside cavity of the cylindrical portion 1 and by an outer wall 6 running parallel with the tubular portion 4 and defining an annular chamber 7 about it.

The wall 6 has two diagrammatically opposite notches 8 formed in its top edge 9.

The edge 9 is covered by a ring 10 which is snap-fastened or stuck or bonded to the head. The ring 10 is made separately for ease of manufacture, but it could be obtained integrally with the sheath.

The ring 10 supports two deformable tabs 11 extending from the vicinity of the edge 9 towards the top edge 12 of the tubular portion 4.

The bottom ends of the tabs 11 are concave so as to act as abutments for the helical spring 5 which is received in the tubular portion 4 and which has previously been compressed axially.

The syringe 13, which is shown in FIG. 2, comprises a body 14, a needle carrier 15 carrying a needle 16, a moving piston (not shown) suitable for sliding inside the body 14, and a piston plunger 17 which projects from the top portion of the syringe and which is terminated by a pusher 18 on which a user can exert force in order to proceed with an injection.

The syringe 13 is put into place in the sheath of FIG. 1 as shown in FIG. 4.

Because the helical spring 5 extends the inside wall of the cylindrical portion 1 of the sheath, the syringe body whose outside diameter is slightly smaller than the inside diameter of the cylindrical portion 1 of the sheath penetrates without difficulty inside the spring and is received within the sheath.

Projecting from the inside wall of its cylindrical portion 1, the sheath has a resilient tab 19 which constitutes a stop against the shoulder constituted by the bottom end 20 of the syringe body 14.

On application of a relatively large amount of force, the stop 19 can be caused to retract and allow the syringe body to pass.

When the collar-forming top edge 21 of the syringe body 14 comes into contact with the resilient tabs of the sheath head and moves these resilient tabs apart, it releases the spring over a short length, with the spring then coming to bear against the collar 21 of the syringe which is situated in the immediate vicinity of the spring.

When the syringe continues to advance towards the injection position, the collar moves the resilient tabs 11 further apart and passes in turn beneath their bottom ends, thereby compressing the spring again within the tubular portion 4.

The resilient tabs 11 return into position above the collar as can be seen in FIG. 7, and they lock the syringe in its injection position inside the sheath.

In this injection position, the needle carrier 15 is flush with the bottom end 2 of the sheath, as can be seen in particular in FIGS. 5 and 6.

A pierced cap 22 is then engaged on the sheath head. This cap 22 is generally cylindrical in shape and is of a diameter which enables it to be received in the annular chamber 7.

The cap has a central bore 23 which allows the pusher 18 of the syringe to pass through, and it has two side notches 24 which extend from its bottom edge 25 and which enable it to engage on either side of the two resilient tabs 11.

As can be seen in FIG. 7, the outside diameter of the cap corresponds to the inside diameter of the ring 10, such that the outwardly directed collar 26 formed on the bottom edge 25 of the cap can penetrate into the head only by deforming towards the inside of the cap by means of a chamfer 27 provided on the collar, but once it has been inserted it cannot escape from the head.

The cap as put into place in this way engages in part around the tubular portion 4 and remains free within the head 3.

As shown in FIG. 8, the device as prepared in this way is ready for use.

The syringe needle which projects from the bottom end of the sheath can be protected by a cover 28.

To inject the substance contained in the syringe the user pushes the pusher 18 so as to move the moving piston inside the body of the syringe.

Because the collar 21 of the syringe body bears against the top edge 12 of the tubular portion 4, the syringe body cannot move down inside the sheath, so the pressure exerted on the pusher 18 causes the piston plunger 17 to be pushed in.

While it is being pushed in, the pusher 18 comes up to the cap 22, and then penetrates into its bore 23, as can be seen in FIG. 9.

As from this instant, the force exerted by the user acts not only on the pusher 18 but also on the cap 22 which is pushed into the head of the sheath together with the pusher.

The effect of this action is to bring the portion of the cap 22 that does not have a notch up to the resilient tabs 11.

As a result, the cap exerts an outwardly-directed force on the two resilient tabs 11, thereby moving them apart, and thus releasing the collar 21 and the helical spring 5.

The syringe body is then held in position only by the force exerted by the user on the pusher.

When the user releases the pressure exerted on the pusher, the helical spring expands and pushes the syringe body together with the pusher 18 and the cap 22 upwards as can be seen in FIG. 10, until the safe position shown in FIG. 11 is reached, where the collar 26 of the cap 22 comes into abutment against the ring 10.

Simultaneously, the shoulder constituted by the bottom edge 20 of the syringe body passes above the tab 19 so that the syringe is prevented from being pushed back into the sheath.

The syringe thus reaches its safe position in which the syringe carrier is withdrawn into the sheath and the needle no longer projects beyond the bottom end 2 of the sheath.

This prevents any risk of accidental contact with the needle.

It can be seen that the device of the invention provides good safety against the problem of accidental contamination.

In addition, it can clearly be seen that the prestress of the spring makes it easier to insert the syringe in the sheath, and in particular makes it possible to automate such insertion.

In particular, the safety device can be delivered with its spring in the prestressed state to a user of the syringe who can easily put prefilled syringes into respective safety devices without needing to make any modification thereto.

Naturally, the embodiment described above is not limiting in any way, and can be modified in any desirable manner without thereby going beyond the ambit of the invention.

What is claimed is:

1. A safety device for a syringe, comprising:
   a body,
   a needle carrier mounted at one end of the body,
   a piston that is axially movable in the body,
   a piston plunger projecting from the body at an end opposite from the needle carrier and suitable for pushing the piston inside the body towards the needle carrier, a sheath in which the syringe body can slide axially between an injection position in which the needle carrier is flush with one end of the sheath and a safe position in which the needle carrier is retracted into the sheath, a helical spring which is axially compressed when the syringe body is in the injection position, said spring then exerting on said body a force tending to cause it to slide into the safe position, the sheath comprising at least one radially movable deformable tab extending substantially longitudinally relative to the sheath and configured to hold the spring in the compressed state even when the syringe body is not in the sheath, a release mechanism comprising a cap sliding in the sheath and which moves inside the sheath towards the resilient tab to move it radially away so as to release at least one of the syringe body and the spring when the piston plunger of the syringe has pushed the piston inside the body into the vicinity of the needle carrier.

2. A device according to claim 1, wherein the helical spring is received inside the sheath in an enlarged portion thereof, around the syringe body, and it bears both against a bearing surface of the sheath and against a collar of the syringe body.

* * * * *